(12) United States Patent
Fukuhara et al.

(10) Patent No.: US 7,582,124 B2
(45) Date of Patent: Sep. 1, 2009

(54) HAIR DYEING COMPOSITION

(75) Inventors: Masaki Fukuhara, Sumida-ku (JP); Takafumi Nishi, Wakayama (JP); Yasuyuki Fujii, Wakayama (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 12/282,272

(22) PCT Filed: Mar. 16, 2007

(86) PCT No.: PCT/JP2007/000234

§ 371 (c)(1),
(2), (4) Date: Sep. 9, 2008

(87) PCT Pub. No.: WO2007/108209

PCT Pub. Date: Sep. 27, 2007

(65) Prior Publication Data

US 2009/0081146 A1 Mar. 26, 2009

(30) Foreign Application Priority Data

Mar. 16, 2006 (JP) ............... 2006-073582
Mar. 16, 2006 (JP) ............... 2006-073584

(51) Int. Cl.
*A61Q 5/10* (2006.01)
*C07D 207/00* (2006.01)
(52) U.S. Cl. .................. 8/405; 8/406; 8/423; 8/435; 8/574; 548/400
(58) Field of Classification Search ........ 8/405, 8/406, 423, 435, 574; 548/400
See application file for complete search history.

(56) References Cited

U.S. PATENT DOCUMENTS

2004/0078905 A1  4/2004  Terranova et al.
2004/0083559 A1  5/2004  Sabelle et al.
2004/0088799 A1  5/2004  Sabelle et al.
2005/0102770 A1* 5/2005  Kiyomine et al. ............ 8/405
2005/0172419 A1  8/2005  Abe et al.

FOREIGN PATENT DOCUMENTS

FR  2 817 474      6/2002
JP  2002 255763    9/2002
WO  2003 051322    6/2003

OTHER PUBLICATIONS

STIC Search Report dated Apr. 15, 2009.*
U.S. Appl. No. 12/281,627, filed Sep. 4, 2008, Fukuhara, et al.

* cited by examiner

*Primary Examiner*—Elisa B Elhilo
(74) *Attorney, Agent, or Firm*—Oblon, Spivak, McClelland, Maier & Neustadt, P.C.

(57) ABSTRACT

Provided is a hair dyeing composition, containing a first part containing (a) a nitrogen-containing compound expressed by the general formula (1) or a salt thereof and a second part containing a component (b) of an oxidizing agent, wherein a pH upon use is 7.5 to 12,

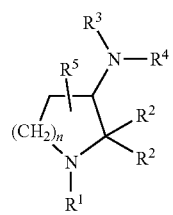

(1)

wherein n=1 or 2, $R^1$ and $R^3$ to $R^5$ represent H, a hydroxy group, and an alkyl group with C12 or less optionally having a substituent, $R^2$ represents a hydroxy group, —R or —OR, in which R means the same as $R^1$ to $R^5$, and two or more of $R^1$ to $R^5$ may be taken together to form a 3 to 8 membered-ring optionally having a substituent.

5 Claims, No Drawings

HAIR DYEING COMPOSITION

FIELD OF THE INVENTION

The present invention relates to a hair dyeing composition that is a two-part hair dye containing a specific nitrogen-containing compound, which gives less damage to the hair and irritation to the scalp during and after treatment, and has excellent hair bleaching ability and hair dyeing ability.

BACKGROUND OF THE INVENTION

An oxidative hair dye composed of the first part containing an alkali agent, a precursor, and a coupler and the second part containing hydrogen peroxide is preferable because gray hair can be more evenly dyed and in that a hair color is greatly changed, as compared to other hair dyes, and thus has been widely used in general. This is derived from characteristics that in an oxidative hair dyes, alkaline hydrogen peroxide decomposes melanin inside hair and a color of the hair can be thus bleached to be brightened. Particularly, in recent years, it has become preferred that black and white hair is dyed without unevenness with more bright colors and with bright and vivid color tone, and there has been a tendency that higher bleaching ability is required.

In order to obtain higher bleaching ability, it is considered that an alkali agent or an oxidizing agent is contained in a large amount, but there is a possibility of causing problems such that, depending on its amount, strong pungent odor is accompanied, hair damage proceeds, and irritation is given to scalp.

Accordingly, a method of containing a specific triazacyclononane compound in hair dyes (Patent Document 1) and a method of containing a specific cyclic amine compound in a hair dye (Patent Document 2) have been proposed. However, these methods are insufficient for obtaining high bleaching ability with less pungent odor and less hair damage.
[Patent Document 1] JP-A-2002-255763
[Patent Document 2] WO Publication No. 2003/051322

SUMMARY OF THE INVENTION

The present invention is to provide a hair dyeing composition, containing a first part containing a component (a) and a second part containing a component (b), wherein a pH upon use is 7.5 to 12:

(a) a nitrogen-containing compound expressed by the following general formula (1) or a salt thereof:

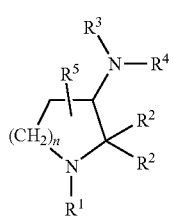

(1)

wherein n denotes an integer of 1 or 2, each of $R^1$ and $R^3$ to $R^5$ independently represents a hydrogen atom, a hydroxy group; or an alkyl group, an alkenyl group, an alkynyl group, a cyclic hydrocarbon group, an aralkyl group or a cyanated alkyl group each having 12 or less carbon atoms; or a 5 to 7 membered-ring saturated or unsaturated heterocyclic group, two of $R^2$ may be the same or different, and each represents a hydroxy group, —R or —OR, wherein R represents an alkyl group, an alkenyl group, an alkynyl group, a cyclic hydrocarbon group, an aralkyl group or a cyanated alkyl group each having 12 or less carbon atoms, or a 5 to 7 membered-ring saturated or unsaturated heterocyclic group, these $R^1$ to $R^5$ may have one or more of substituents selected from a hydroxy group, an amino group; and an alkyl group, a cyclic hydrocarbon group, an aralkyl group, a heteroaryl group, an alkoxy group, an ester group, and a cyanated alkyl group each having 8 or less carbon atoms, two or more of $R^1$ to $R^5$ may be taken together to form a saturated or an unsaturated 3 to 8 membered-ring, and the ring may have a substituent selected from a hydroxy group, and an alkyl group and a cyclic hydrocarbon group which have 12 or less carbon atoms and optionally may have a substituent; and (b) an oxidizing agent.

MODE FOR CARRYING OUT THE INVENTION

The present invention relates to a hair dyeing composition excellent in hair bleaching ability and having less hair damage.

The present inventors found that, by containing a nitrogen-containing compound having a specific structure or a salt thereof in a hair dyeing composition, an alkali agent and an oxidizing agent can be efficiently worked inside hair and bleaching ability and hair dyeing ability can be thus improved, or amounts of the alkali agent and the oxidizing agent can be reduced without lowering the bleaching ability and hair dyeing ability, and hair damage and irritation to the scalp can be reduced.

In the present invention, a "hair dye" includes hair bleaches without containing dyes in addition to hair coloring agents containing dyes. Further, "dyeing the hair" means dyeing the hair as well as bleaching the hair in a hair dye containing a dye, and means bleaching the hair in a bleach without containing a dye. The hair dye of the present invention forms a two-part type composed of the first part containing an alkali agent and the second part containing an oxidizing agent, and the "whole composition" in the present invention refers to the whole of composition immediately before using the mixture of the first part and the second part.

In a nitrogen-containing compound represented by the general formula (1) (hereinafter, referred to as a nitrogen-containing compound (1)) of a component (a) used in the present invention, examples of a saturated or unsaturated 3 to 8 membered-ring which is formed by taking a plurality of substituents together include a pyrrolidine ring, a piperidine ring, a cyclohexane ring, a cyclopropane ring, and a pyrrole ring. As a combination of substituents taking together to form such a ring, a combination of $R^3$ and $R^4$ and a combination of two of $R^2$ are preferable, and a combination of $R^3$ and $R^4$ is more preferable.

In Rs in $R^1$, $R^3$ to $R^5$ and $R^2$, examples of the alkyl group having 12 or less carbon atoms include a methyl group, an ethyl group, a propyl group, an isopropyl group, an n-butyl group, a sec-butyl group, and a tert-butyl group; examples of the alkenyl group having 12 or less carbon atoms include an aryl group, a 2-propenyl group, a 3-methyl-2-butenyl group, and a 3-butenyl group; examples of the alkynyl group having 12 or less carbon atoms include an ethynyl group, 2-propynyl group, 2-butenyl group, and 3-butynyl group; examples of the cyclic hydrocarbon group having 12 or less carbon atoms include a cyclopropyl group, a cyclopentyl group, a cyclohexyl group, a phenyl group, a tolyl group, and a xylyl group; examples of the aralkyl group having 12 or less carbon atoms include a benzyl group, an α-methylbenzyl group, and a phenethyl group; and examples of the cyanated alkyl group having 12 or less carbon atoms include a cyanated methyl group, a 2-cyanated ethyl group, and 3-cyanated propyl group. Further, examples of the 5 to 7 membered-ring saturated or unsaturated heterocyclic group include a pyrrolidinyl group, piperidyl group, a furyl group, a pyridyl group, and a morpholyl group.

Examples of the —OR group in $R^2$ include a methoxy group, an ethoxy group, a propoxy group, an isopropoxy group, a cyclohexyloxy group, a cyclopentyloxy group, a benzyloxy group, and a phenoxy group.

These $R^1$ to $R^5$ may further have substituents, and examples of such substituents include a hydroxy group, an amino group and an alkyl group, a cyclic hydrocarbon group, an aralkyl group, a heteroaryl group, alkoxy group, an ester group, a mono- or dialkylamino group and a cyanated alkyl group each having 8 or less of carbon atoms. Among these, preferable examples are a hydroxy group, a dimethylamino group, a methoxy group, an ethoxy group, a propoxy group, an isopropoxy group, a phenyl group, a tolyl group, and a cyclohexyl group. Note that "12 or less carbon atoms" in $R^1$ to $R^5$ means the number including substituents which may be further contained therein.

As a substituent on a ring formed by taking two or more of $R^1$ to $R^5$ together, an alkyl group and a cyclic hydrocarbon group are preferable. Specifically, examples of the alkyl group include a methyl group, an ethyl group, a propyl group, and an isopropyl group, an n-butyl group, a sec-butyl group, a tert-butyl group, an n-pentyl group, a 2-ethylhexyl group, and an n-hexyl group; examples of the cyclic hydrocarbon group include a cyclopropyl group, a cyclopentyl group, a cyclohexyl group, a phenyl group, a tolyl group, and a xylyl group.

In view of stability of a hair coloring agent in particular, the nitrogen-containing compound (1) is preferably a nitrogen-containing compound in which, in the general formula (1), $R^1$ represents a hydrogen atom, or an alkyl group or a cyclic hydrocarbon group each having 12 or less carbon atoms, two of $R^2$ represent the same or different alkyl group or cyclic hydrocarbon group each having 12 or less carbon atoms, $R^3$ and $R^4$ each independently represents a hydrogen atom, or an alkyl group or a cyclic hydrocarbon group each having 12 or less carbon atoms, or both are taken together to form a saturated 5 or 6 membered-ring containing a nitrogen atom, and $R^5$ represents a hydrogen atom, a hydroxy group, or alkyl group or a cyclic hydrocarbon group each having 12 or less carbon atoms.

Examples of a preferable nitrogen-containing compound (1) used in the present invention are shown in the following:

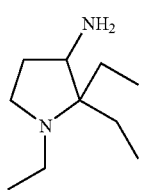

1-I-1

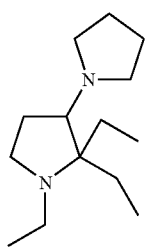

1-I-2

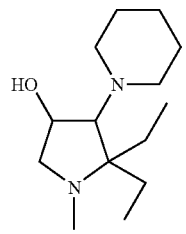

1-I-3

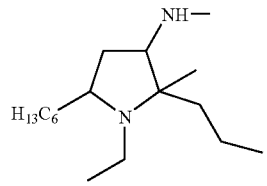

1-I-4

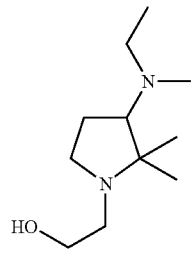

1-I-5

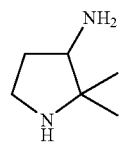

1-I-6

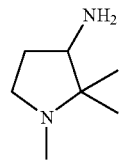

1-I-7

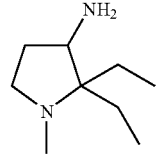

1-I-8

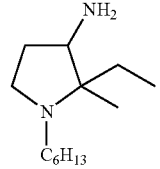

1-I-9

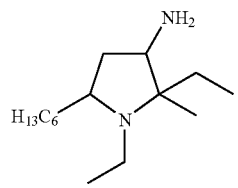

1-I-10

-continued
1-I-11 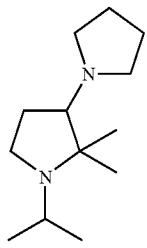
1-I-12 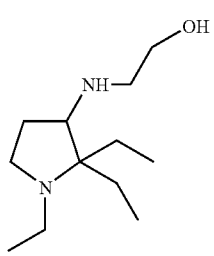
1-I-13 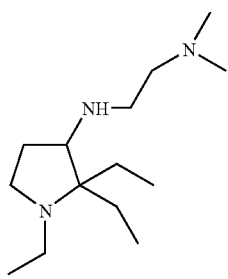
1-I-14 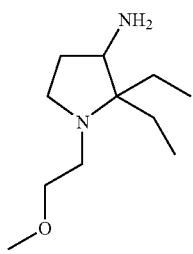
1-I-15 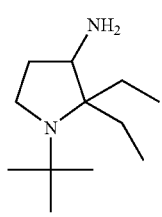
•In the case of n = 1 in the general formula (1)
1-II-1 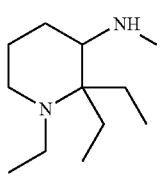
-continued
1-II-2 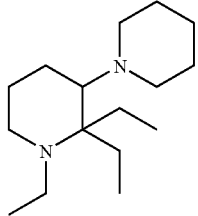
1-II-3 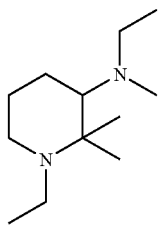
1-II-4 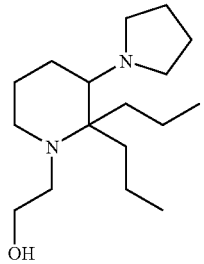
1-II-5 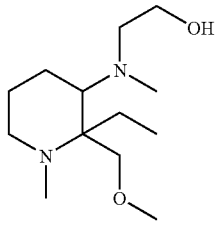
1-II-6 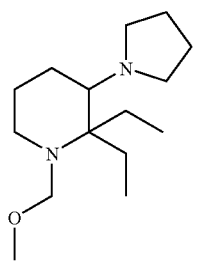
1-II-7 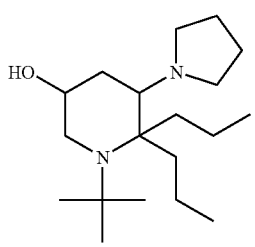
1-II-8 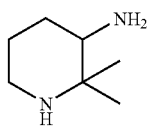

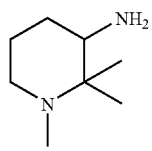
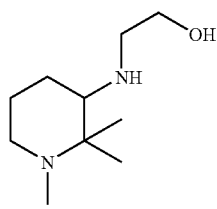
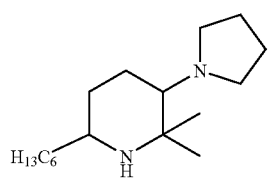
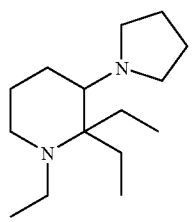
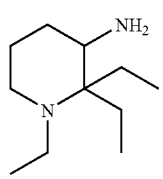
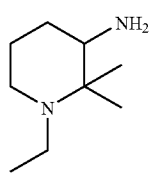
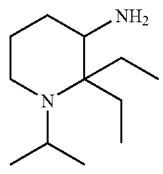
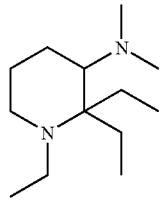
1-II-9
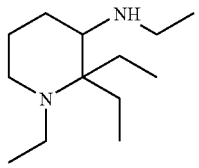
1-II-10
• In the case of n = 2 in the general formula (1)
1-II-11
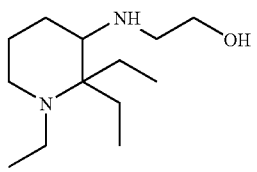
1-II-12
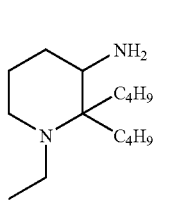
1-II-13
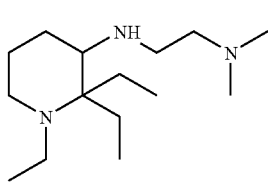
1-II-14
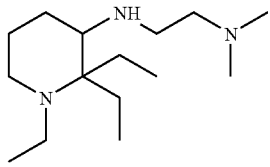
1-II-15
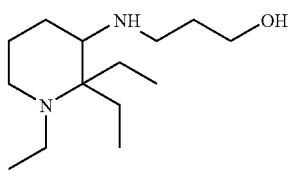
1-II-16
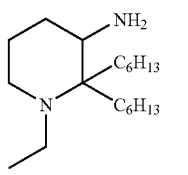
1-II-17
1-II-18
1-II-19
1-II-20
1-II-21
1-II-22
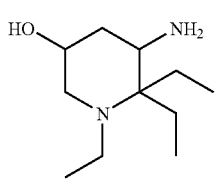
1-II-23
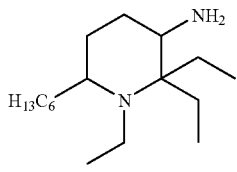
1-II-24

-continued

1-II-25
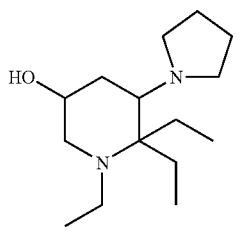

1-II-26
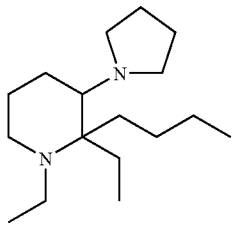

1-II-27
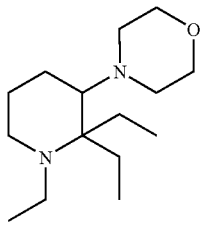

1-II-28
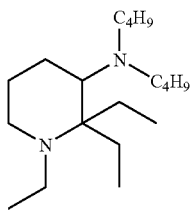

1-II-29
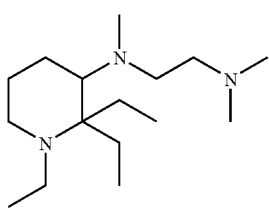

1-II-30
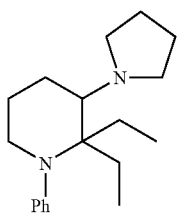

When the nitrogen-containing compound (1) has an asymmetric carbon atom, any of (S) form and (R) form, or a mixture of the both forms may be acceptable. A salt of the nitrogen-containing compound (1) preferably includes, for example, a salt with inorganic acids or organic acids such as hydrochloric acid, sulfuric acid, phosphoric acid, acetic acid, propionic acid, lactic acid, citric acid, succinic acid, hydrobromic acid, hydriodic acid, methane sulfonic acid, methyl sulfuric acid, and perchloric acid.

The nitrogen-containing compound (1) used in the present invention can be produced by combining known reactions. For example, the compound (1) can be produced as follows.

An azethizine-2-carboxylic acid derivative or a proline derivative in which a carboxy group is esterified is used as a starting material, and a carbonyl group is alkylated using a Grignard reagent or the like, and a newly generated hydroxy group is then halogenated, thereafter aminating the resultant using an amine derivative to thereby cause a ring expansion reaction at the same time when halogen is substituted, and thus the desired nitrogen-containing compound can be obtained.

Hereinafter, the production method of the nitrogen-containing compound (1) is shown in reaction schema 1, 2 and 3 with reference to an example when the nitrogen-containing compound (1) is a pyrrolidine derivative (when n denotes 2 in the general formula (1)).

[Reaction schema 1]

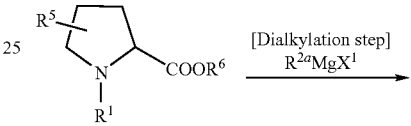

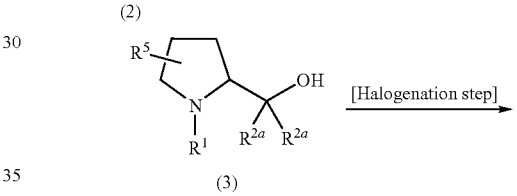

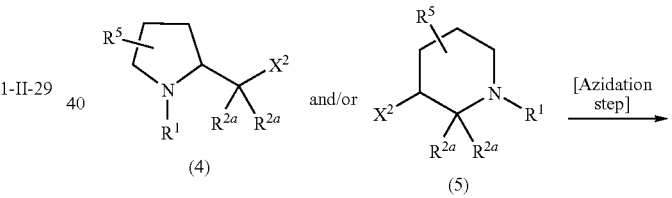

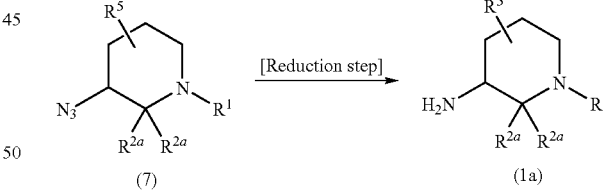

[Reaction schema 2]

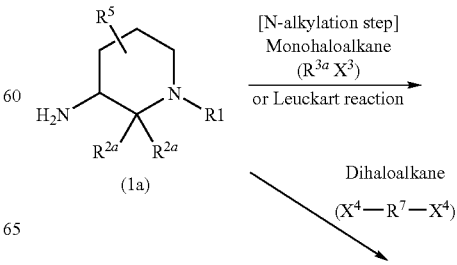

-continued

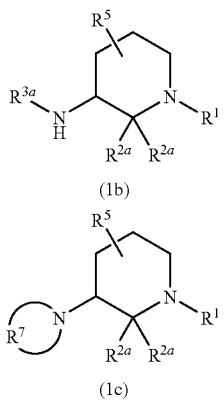

(1b)

(1c)

[Reaction schema 3]

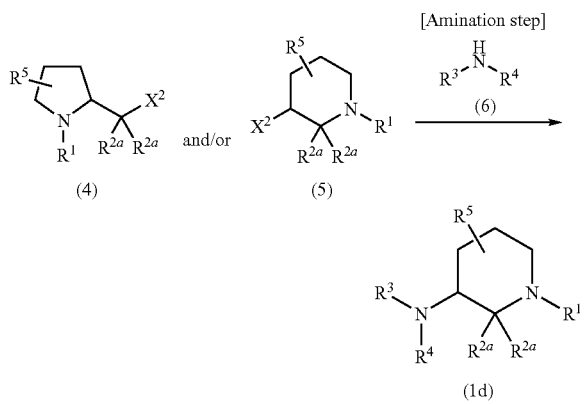

(in the formula $R^1$ and $R^6$ represent hydrogen atoms, or alkyl groups or cyclic hydrocarbon groups each having 1 to 12 carbon atoms, and two of $R^{2a}$ may be the same or different, and represent alkyl groups or cyclic hydrocarbon groups each having 1 to 12 carbon atoms, $R^{3a}$ represents an alkyl group or a cyclic hydrocarbon group each having 1 to 12 carbon atoms, $R^{4a}$ represents an alkyl group having 1 to 12 carbon atoms, $R^7$ represents an alkylene group having 2 to 12 carbon atoms, $R^3$ and $R^4$ represent hydrogen atoms, or alkyl groups or cyclic hydrocarbon groups each having 1 to 12 carbon atoms, or $R^3$ and $R^4$ are taken together with the adjacent nitrogen atom to form a ring structure, $R^5$ represents a hydrogen atom, a hydroxy group, or an alkyl group or a cyclic hydrocarbon group each having 1 to 12 carbon atoms, and $X^1$, $X^2$, $X^3$ and $X^4$ represent halogen atoms.)

In the method shown in the reaction schema 1, a proline derivative (2) whose synthesis method has been known (JP-A-7-103098) is used as a raw material, a 3-amino-2,2-dialkylpiperidine derivative (1a) in which $R^3$ and $R^4$ are hydrogen atoms in the general formula (1) can be produced by undergoing the total four steps.

In the method shown in the reaction schema 2, a piperidine derivative (1a) obtained in the reaction schema 1 is used as a raw material, a piperidine derivative (1b) in which $R^3$ is an alkyl group or a cyclic hydrocarbon group each having 1 to 12 carbon atoms and $R^4$ is a hydrogen atom in the general formula (1) can be produced by one step using monohaloalkane or a Leuckart reaction. Alternatively, using the piperidine derivative (1a) obtained in the reaction schema 1 as a raw material in the same manner, a piperidine derivative (1c) in which $R^3$ and $R^4$ are taken together with the adjacent nitrogen atom to form a cyclic structure in the general formula (1) can be produced in one step using dihaloalkane.

Also, in a method shown in the reaction schema 3, using halide (4) or (5) obtained in the reaction schema 1 as a raw material, a piperidine derivative (1d) in which $R^3$ and $R^4$ are hydrogen atoms, alkyl groups or cyclic hydrocarbon groups each having 1 to 12 carbon atoms, or are taken together with the adjacent nitrogen atom to form a cyclic structure in the general formula (1) can be produced by undergoing the amination step.

[Reaction Schema 1]

Dialkylation Step

A proline derivative (2) as a raw material whose synthesis method has been known has at least one asymmetric carbon, and each asymmetric carbon may be optically active or may be a racemic body. Alternatively, it may be a mixture with any ratio thereof.

Alkyl magnesium halide used in this step is expressed by $R^{2a}MgX^1$. $R^{2a}$ corresponds to $R^2$ in the general formula (1), and the same groups described as specific examples of $R^2$ are included. Examples of a halogen atom expressed by $X^1$ include a chlorine atom, a bromine atom, and an iodine atom.

An amount of alkyl magnesium halide to be used is preferably in the range of 2 to 30 times by mole, and more preferably 3 to 5 times by mole based on the proline derivative (2) that is a raw material.

As a reaction solvent, a solvent generally used in an organic synthesis using an organic metal compound, for example, ether solvents such as diethyl ether, tetrahydrofuran, and dioxane, aromatic solvents such as benzene, toluene and xylene, and halogen solvents such as chloroform and dichloromethane, hydrocarbon solvents such as heptane and hexane, or mixtures thereof can be used. Generally, diethyl ether, tetrahydrofuran, and toluene are preferable in view of handling.

A reaction temperature is preferably in the range of $-20°$ C. to a solvent reflux temperature, and a reaction is performed under ordinary pressure, but if necessary, the reaction may be performed in a pressurized condition or a reduced pressure condition.

As a post treatment and a purification step after the reaction, filtration, extraction, drying, recrystallization, distillation under reduced pressure, column purification, and the like can be performed, but these may be selected according to necessity, and it is possible to proceed to a next step without carrying out the purification step in some cases.

Halogenation Step

Examples of a halogenating agent used in this step include acid halides such as methane sulfonyl chloride, and p-toluene sulfonyl chloride, and thionyl chloride, phosphorus pentachloride, phosphorus trichloride, and phosphorus tribromide.

When an acid halide such as methane sulfonyl chloride and p-toluene sulfonyl chloride is used as a halogenating agent, it is preferable to suitably combine and use organic amines such as triethylamine, pyridine and dimethylaminopyridine, and alkali agents such as inorganic alkali compounds, for example, sodium hydroxide and potassium carbonate, and it is more preferable to combine and use organic amines.

An amount of a halogenating agent to be used is preferably in the range of 1 to 10 times by mole based on the prolinol derivative (3) that is a raw material, and more preferably in the range of 1 to 2 times by mole.

When an acid halide such as methane sulfonyl chloride and p-toluene sulfonyl chloride is used as a halogenating agent, an amount of an alkali agent to be combined upon use is in the range of 1 to 10 times by mole based on the prolinol derivative (3) that is a raw material, and more preferably in the range of 1 to 2 times by mole.

Further, in this step, halogenation can be also performed by using triphenyl phenyl phosphine and tetrahalomethane such as carbon tetrabromide in combination.

As a reaction solvent, although being different depending on a halogenating agent to be used, solvents generally used in organic synthesis, for example, alcohol solvents such as methanol, ethanol, and 2-propanol, ether solvents such as diethyl ether, tetrahydrofuran, and dioxane, aromatic solvents such as benzene, toluene, and xylene, halogen solvents such as chloroform and dichloromethane, acetonitrile, DMF, DMSO, N-methyl pyrrolidone, and water, or a mixture thereof can be used. In general, dichloromethane, chloroform and toluene are preferable from the viewpoint of handling.

A reaction temperature is preferably in the range of −20° C. to a solvent reflux temperature, and more preferably in the range of −20° C. to a room temperature from the viewpoint of selectivity. The reaction is carried out under ordinary pressure but may be preformed under pressurized condition or reduced pressure condition if necessary.

As a post treatment and a purification step after the reaction, filtration, extraction, drying, recrystallization, distillation under reduced pressure, column purification, and the like can be performed, and these may be selected according to necessity, and it is possible to proceed to a next step without carrying out the purification step in some cases.

Azidation Step

Examples of an azidating agent used in this step include an azide metal reagent such as sodium azide, and trimethylsilane azide. In general, sodium azide is preferable from the viewpoint of handling.

An amount of an azidating agent to be used is preferably in the range of 1 to 20 times by mole based on 2-halo(dialkylmethyl)pyrrolidine (4) or 3-halo-2,2-dialkyl piperidine (5), and more preferably in the range of 1 to 3 times by mole.

As a reaction solvent, although being different depending on an azidating agent to be used, solvents generally used in organic synthesis, for example, alcohol solvents such as methanol, ethanol, and 2-propanol, ether solvents such as diethyl ether, tetrahydrofuran, and dioxane, aromatic solvents such as benzene, toluene, and xylene, halogen solvents such as chloroform and dichloromethane, acetonitrile, DMF, DMSO, N-methyl pyrrolidone, and water, or a mixture thereof can be used. In general, DMF and dichloromethane are preferable from the viewpoint of handling.

A reaction temperature is preferably in the range of −20° C. to a solvent reflux temperature. The reaction is carried out under ordinary pressure but may be preformed under pressurized condition or reduced pressure condition if necessary.

As a post treatment and a purification step after the reaction, filtration, extraction, drying, recrystallization, distillation under reduced pressure, column purification, and the like can be performed, and these may be selected according to necessity, and depending on cases, it is possible to proceed to a next step without carrying out the purification step.

Reduction Step

This step can be performed by a hydrogenation reaction using a transfer metal catalyst. Examples of the transfer metal catalyst include Pd based catalysts such as Pd/C, Ru based catalysts such as Ru/C, Ru/Al$_2$O$_3$, and RuO$_2$, Rh based catalysts such as Rh/C and Rh/Al$_2$O$_3$, and Pt based catalysts such as Pt/C and PtO$_2$, and Ni based catalysts such as Raney nickel. Among these, Pd/C is preferable from the viewpoint of yield. These catalysts can be used alone or two or more kinds thereof can be used in combination.

An amount of a transfer metal catalyst to be used is preferably in the range of 0.05 to 50% by mass based on the azide product (7), and more preferably in the range of 1 to 20% by mass from the viewpoint of handling.

As a reaction solvent, solvents generally used in organic synthesis, for example, alcohol solvents such as methanol, ethanol, and 2-propanol, ether solvents such as diethyl ether, tetrahydrofuran, and dioxane, aromatic solvents such as benzene, toluene, and xylene, halogen solvents such as chloroform and dichloromethane, acetonitrile, DMF, DMSO, N-methylpyrrolidone, and water, or mixture thereof can be used. In general, DMF and dichloromethane are preferable from the viewpoint of handling.

A hydrogenation reaction can be generally performed in the range of −20° C. to 250° C., preferably at a comparatively mild temperature, for instance, at 20° C. to 120° C., more preferably at 20° C. to 80° C. A pressure during the hydrogenation reaction is generally at an ordinary pressure to 25 MPa, and preferably at an ordinary pressure to 15 MPa.

Further, in this step, reduction may be carried out also with a hydrogenation reagent such as lithium aluminum hydride (LiAlH$_4$) and sodium aluminum hydride (NaAlH$_4$).

As a post treatment and a purification step after the reaction, filtration, extraction, drying, recrystallization, distillation under reduced pressure, column purification, and the like can be performed, and these may be selected according to necessity, and depending on cases, it is possible to proceed to a next step without carrying out the purification step.

[Reaction Schema 2]

N-Alkylation Step (by Mono- or Dihaloalkane)

Examples of an alkylating agent in this step include monohaloalkanes such as methane chloride, methane bromide, methane iodide, ethane bromide, n-propane chloride, n-propane bromide, isopropane bromide, n-butane bromide, t-butane bromide, n-hexane chloride, n-hexane bromide, n-hexane iodide, cyclohexane bromide, n-octane bromide, n-dodecane bromide, n-dodecane iodide, 2-bromoethanol, 6-bromohexanol, and 2-chloroethyl methyl ether; and dihaloalkanes such as 1,3-dichloropropane, 1,3-dibromopropane, 1,4-dichlorobutane, 1,4-dibromobutane, 1,4-diiodobutane, 1,5-dibromopentane, 1,4-dibromopentane, 1,6-dibromohexane, and 2,5-dibromohexane.

When monohaloalkane or dihaloalkane is used as an alkylating agent, it is preferable to add an alkali agent. Examples of the alkali agent include inorganic alkali compounds such as sodium hydrogen carbonate, sodium carbonate, potassium carbonate, calcium carbonate, cesium carbonate, sodium hydroxide, and potassium hydroxide; and organic amine compounds such as triethylamine, pyridine, and N-methylmorpholine. From the viewpoint of yield, inorganic alkali compounds such as sodium hydrogen carbonate, sodium carbonate, and potassium carbonate are preferable.

An amount of an alkylating agent to be used is preferably in the range of 1 to 30 times by mole, more preferably in the range of 1 to 10 times by mole and even more preferably in the range of 1 to 5 times by mole based on 3-amino-2,2-dialkylpiperidine derivative (1a).

An amount of an alkali agent to be used differs depending on an alkali agent to be used, but is preferably in the range of 1 to 30 times by mole, and more preferably 1 to 10 times by mole based on 3-amino-2,2-dialkylpiperidine derivative (1a).

Alkylation can be achieved by performing reduction of an amide group after amidating an amino group in a 3-amino-2,2-dialkylpiperidine derivative (1a) with an acylating agent.

As a reaction solvent, although being different depending on an alkylating agent and an alkali agent to be used, solvents generally used in organic synthesis, for example, alcohol solvents such as methanol, ethanol, and 2-propanol, ether solvents such as diethyl ether, tetrahydrofuran, and dioxane, aromatic solvents such as benzene, toluene, and xylene, halogen solvents such as chloroform and dichloromethane, acetonitrile, DMF, DMSO, N-methylpyrrolidone, and water, or a mixture thereof can be used. In general, toluene, chloroform and dichloromethane are preferable from the viewpoint of handling.

A reaction temperature is preferably in the range of –20° C. to a solvent reflux temperature, and a reaction is performed under ordinary pressure, but may be performed in a pressurized condition or a reduced pressure condition if necessary.

As a post treatment and a purification step after the reaction, filtration, extraction, drying, recrystallization, distillation under reduced pressure, column purification, and the like can be performed, but these may be selected according to necessity.

N-Alkylation Step (by Leuckart Reaction)

N-alkylation (in particular, N-methylation) in this step can be performed by a Leuckart reaction using aldehydes such as formaldehyde and a reducing agent such as formic acid.

An amount of aldehyde to be used is in the range of to 30 times by mole, and more preferably in the range of 1 to 10 times by mole based on 3-amino-2,2-dialkylpiperidine derivative (1a).

An amount of a reducing agent to be used is in the range of 1 to 30 times by mole, and more preferably in the range of 1 to 10 times by mole based on 3-amino-2,2-dialkylpiperidine derivative (1a).

As a reaction solvent, although being different depending on an alkylating agent and an alkali agent to be used, solvents generally used in organic synthesis, for example, alcohol solvents such as methanol, ethanol, and 2-propanol, ether solvents such as diethyl ether, tetrahydrofuran, and dioxane, aromatic solvents such as benzene, toluene, and xylene, halogen solvents such as chloroform and dichloromethane, acetonitrile, DMF, DMSO, N-methylpyrrolidone, and water, or a mixture thereof can be used. Alternatively, the reaction can be carried out without a solvent in some cases. In general, water, ethanol and toluene are preferably used as a reaction solvent from the viewpoint of handling.

A reaction temperature is preferably in the range of –20° C. to a solvent reflux temperature, and the reaction is performed under ordinary pressure, but may be performed in a pressurized condition or a reduced pressure condition if necessary.

As a post treatment and a purification step after the reaction, filtration, extraction, drying, recrystallization, distillation under reduced pressure, column purification, and the like can be performed, but these may be selected according to necessity.

Reaction Schema 3: Amination Step

Amine used in this step is expressed by the following general formula (6):

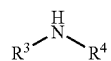

(6)

(in the formula, $R^3$ and $R^4$ express the same meaning as the above.)

In the general formula (6), $R^3$ and $R^4$ preferably denote hydrogen atoms, alkyl groups having 1 to 4 carbon atoms, or pyrrolidine rings or piperidine rings forming rings.

Specific examples of amine (6) used in this step include ammonia, methylamine, ethylamine, n-propylamine, isopropylamine, n-butylamine, isobutylamine, sec-butylamine, t-butylamine, n-hexylamine, cyclohexylamine, n-octylamine, n-decylamine, n-dodecylamine, aniline, monoethanolamine, 2-(2-aminoethoxy)ethanol, N,N-dimethylethylenediamine, dimethylamine, N-ethylmethylamine, diethylamine, diisopropylamine, diisobutylamine, dicyclohexylamine, bis(2-ethylhexyl)amine, didecylamine, diethanolamine, diisopropanolamine, N,N-dimethyl-N'-ethylethylenediamine, pyrrolidine, piperidine, hexamethyleneimine, 2-pyrrolidinemethanol, 2-piperidinemethanol, piperazine, and ethyl piperazine.

An amount of amine (6) to be used is preferably in the range of 1 to 30 times by mole, and more preferably in the range of 1 to 10 times by mole based on 2-[halo(dialkylmethyl)pyrrolidine (4) or 3-halo-2,2-dialkylpiperidine (5).

Further, in this step, depending on amine used as an aminating agent, it is preferable to add an alkali agent. Examples of the alkali agent include inorganic alkali compounds such as sodium hydrogen carbonate, sodium carbonate, potassium carbonate, calcium carbonate, cesium carbonate, sodium hydroxide, and potassium hydroxide, and organic amine compounds such as triethylamine, pyridine, and N-methylmorpholine.

An amount of an alkali agent to be used is preferably in the range of 1 to 30 times by mole, and more preferably in the range of 1 to 10 times by mole based on 2-[halo (dialkylmethyl)pyrrolidine (4) or 3-halo-2,2-dialkylpiperidine (5).

As a reaction solvent, solvents generally used in organic synthesis, for example, alcohol solvents such as methanol, ethanol, and 2-propanol, ether solvents such as diethyl ether, tetrahydrofuran, and dioxane, aromatic solvents such as benzene, toluene, and xylene, halogen solvents such as chloroform and dichloromethane, acetonitrile, DMF, DMSO, N-methylpyrrolidone, and water, or a mixture thereof can be used. Alternatively, the reaction can be carried out without a solvent in some cases. In general, chloroform, dichloromethane, and toluene are preferable from the viewpoint of handling.

As a post treatment and a purification step after the reaction, filtration, extraction, drying, recrystallization, distillation under reduced pressure, column purification, and the like can be performed, and these may be selected according to necessity.

As described above, with reference to examples wherein a nitrogen-containing compound (1) or a salt thereof is a pyrrolidine derivative (n=2 in the general formula (1)), production methods thereof have been explained, and in the case where the nitrogen-containing compound (1) or a salt thereof is a piperidine derivative (n=1 in the general formula (1)), it can be also produced according to the above described methods.

The nitrogen-containing compound (1) or a salt thereof being a component (a) can be used in at least one kind, and a content thereof is preferably 0.01 to 20% by weight in the whole composition, more preferably 0.02 to 10% by weight, even more preferably 0.05 to 8% by weight, and even more preferably 0.1 to 5% by weight from the viewpoint of sufficient bleaching and hair dyeing effect.

Examples of an oxidizing agent of the component (b) include hydrogen peroxide and hydrogen peroxide generating agents such as urea peroxide, melamine peroxide, sodium perborate, potassium perborate, sodium percarbonate, and potassium percarbonate, and among these, hydrogen peroxide is preferable. A content of an oxidizing agent is, as in hydrogen peroxide, preferably 0.1 to 12% by weight in the whole composition, more preferably 0.5 to 9% by weight, and even more preferably 1 to 6% by weight from the viewpoints of sufficient bleaching and hair dyeing effect, and reduction of hair damage and scalp irritation.

If the hair dyeing composition of the present invention further contains one or more kinds of chelating agents whose use in a hair dyeing composition has been known, such as ethylenediamine tetraacetate, ethylenediamine hydroxyethyl triacetic acid and diethylenetriamine pentaacetic acid, or salts thereof as a component (c), it is preferable because an oxidizing agent and an alkali agent are efficiently reacted in hair. A content of these chelating agents is preferably in the range of 0.01 to 5% by weight in the whole composition from the viewpoint of a sufficient bleaching and hair dyeing effect. These chelating agents can be incorporated in one of the first part and the second part, or in the both thereof.

The present invention can achieve more effective bleaching and dyeing by using the component (a) with an alkali agent. Examples of an alkali agent that can be used include ammonia, alkanolamines such as monoethanolamine, isopropanolamine, 2-amino-2-methylpropanol, and 2-aminobutanol, alkanediamine such as 1,3-propanediamine, carbonate salts such as ammonium carbonate, ammonium hydrogen carbonate, guanidine carbonate, sodium carbonate, potassium carbonate, sodium hydrogen carbonate, and potassium hydrogen carbonate. Among these, ammonia and alkanolamines are preferable, and among alkanolamines, monoethanolamine is more preferable. These alkali agents can be used alone or in two or more kinds thereof in combination and contained in the first part. The content thereof can be suitably selected within the range satisfying necessity of pH, and is preferably 0.05 to 10% by weight in the whole composition, more preferably 0.1 to 5% by weight, and even more preferably 0.2 to 3% by weight from the viewpoints of a sufficient bleaching and hair dyeing effect and reduction of hair damage and scalp irritation.

When the composition of the present invention is a hair dye containing a dye, an oxidative dye intermediate or a direct dye is contained in the first part as dye. When the composition of the present invention is a hair bleach, these dyes are not contained therein.

As an oxidative dye intermediate suitable for the hair dyeing composition of the present invention, known precursors and couplers which are generally used as a hair dye can be used.

Examples of the precursor include paraphenylenediamine, toluene-2,5-diamine, 2-chloroparaphenylenediamine, paraminophenol, paramethylaminophenol, ortho-aminophenol, 2,4-diaminophenol and N-phenylparaphenylenediamine, and salts thereof.

Examples of the coupler include metaphenylenediamine, 2,4-diaminophenoxyethanol, metaminophenol, 2-methyl-5-aminophenol, 2-methyl-5-(2-hydroxyethylamino)phenol, resorcin, 1-naphthol, 1,5-dihydroxynaphthalene and hydroquinone, and salts thereof.

The precursors and couplers can be respectively used alone or in two or more kinds thereof in combination, and the content thereof is each preferably 0.01 to 5% by weight, and more preferably 0.1 to 4% by weight of the whole composition.

On the other hand, as a direct dye, known acid dyes, basic dyes, disperse dyes, and reactive dyes which are available for a hair dye can be used. Examples of the acid dyes include blue No. 1, violet No. 401, black No. 401, orange No. 205, red No. 227, red No. 106, yellow No. 203, and acid orange 3. Examples of the basic dyes include basic blue 99, basic brown 16, basic brown 17, basic red 76, and basic yellow 57. Examples of the direct dyes except for acid dyes and basic dyes include 2-nitroparaphenylenediamine, 2-amino-6-chloro-4-nitrophenol, 3-nitroparahydroxyethylaminophenol, 4-nitro-ortho-phenylenediamine, 4-amino-3-nitrophenol, 4-hydroxypropylamino-3-nitrophenol, N,N-bis-(2-hydroxyethyl)-2-nitroparaphenylenediamine, disperse violet 1, disperse blue 1, disperse black 9, HC blue 2, HC orange 1, HC red 1, HC red 3, HC yellow 2, HC yellow 4, and HC yellow 5.

These direct dyes can be used alone or in combination of two or more kinds thereof, and the content thereof is preferably 0.001 to 5% by weight, and more preferably 0.01 to 4% by weight in the whole composition. Alternatively, an oxidative dye intermediate and a direct dye can be used in combination, and in this case, a total amount of the oxidative dye intermediate and the direct dye is preferably 0.05 to 10% by weight, and more preferably 0.1 to 8% by weight in the whole composition.

The hair dyeing composition of the present invention can further contain a conditioning component. The conditioning component may be those used as cosmetics, and the hair dyeing composition contains soluble or dispersible polymers or oils. These conditioning components are attached to hair when diluted with water at the time of hair conditioning treatment or washing hair with shampoo after hair dyeing treatment, thereby a conditioning effect can be further improved.

Examples of preferable conditioning components used in the hair dyeing composition of the present invention include silicones, organic conditioning oils (e.g., hydrocarbon oil, polyolefin, aliphatic esters, and aliphatic amides), and a conditioning polymer. A content of these conditioning components is preferably 0.01 to 20% by weight in the whole composition, more preferably 0.05 to 15% by weight, and even more preferably 0.5 to 5% by weight.

Examples of the silicones are shown in the following. (Silicones-1) dimethicone, dimethiconol, cyclomethicone Silicone expressed by the general formula (8) below is exemplified:

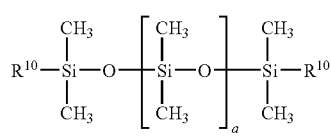

(8)

(in the formula, $R^{10}$ denotes a methyl group or a hydroxy group, or two of $R^{10}$ may form one oxygen atom to constitute a ring, and a denotes a number of 1 to 20,000.)

Examples thereof include BY11-026, BY22-19, and FZ-3125, which are all made by Dow Corning Toray Co., Ltd. Further, higher polymerized dimethylpolysiloxane can be used in a form of being dissolved or dispersed in a liquid oil (e.g., (i) lower polymerized dimethylpolysiloxane, or (ii) liquid silicone oil such as cyclomethicone, or liquid hydrocarbon oil such as isoparaffin)

(Silicones-2) Amino-Modified Silicones

Various amino-modified silicones can be used, but in particular, amino-modified silicones expressed by the general formula (9) and having an average molecular weight of about 3,000 to 100,000, which are known as the INCI name of amodimethicone, are preferable.

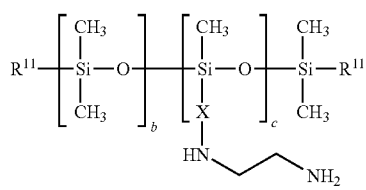

(9)

(in the formula, $R^{11}$ denotes a methyl group or a hydroxy group, X denotes a bivalent hydrocarbon group having 2 to 6 carbon atoms, and b and c denote numbers of 1 to 20,000.)

This amino-modified silicone is preferably used as an aqueous emulsion liquid, and examples of commercially available products thereof include SM8704C (made by Dow Corning Toray Co., Ltd.) and DC 929 (made by Dow Corning Co., Ltd.).

Examples of other amino-modified silicones include bis (C13-15 alkoxy)PG amodimethicone expressed by the following general formula (10), and as a commercially available product thereof, include 8500 Conditioning Agent (Dow Corning Co., Ltd.).

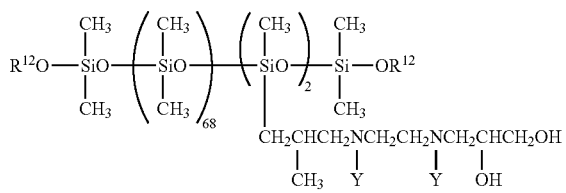

(10)

(in the formula, $R^{12}$ denotes a linear or branched chain alkyl group having 13 to 15 carbon atoms, and 75% of Ys denote —$CH_2CH(OH)CH_2OH$ group and 25% denote hydrogen atoms.)

Furthermore, amino-modified silicone to be a copolymer containing a polyoxyalkylene block in a main chain can be also used, and an example thereof includes bisisobutyl PEG-15/amodimethicone expressed by the general formula (11).

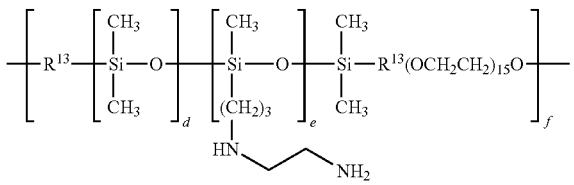

(11)

(in the formula, $R^{13}$ denotes an isobutylene group, d denotes a number of two or more, preferably a number of 2 to 1,000, e denotes a number of one or more, preferably a number of 1 to 50, and f denotes a number of two or more, preferably a number of 2 to 100).

Examples of commercially available products thereof include FZ-3789 and silicone SS-3588 (made by Dow Corning Toray Co., Ltd.).

(Silicones-3) Polyether-Modified Silicones

Various polyether-modified silicones can be used, but preferable are polyether-modified silicones expressed by the general formula (12) and known as the INCI name as PEG-n dimethicones having an average molecular weight of 3,000 to 100,000, in which a part of a methyl group in dimethicone is substituted with polyethylene glycol (for example, PEG-3 dimethicone, PEG-7 dimethicone, PEG-8 dimethicone, PEG-9 dimethicone, PEG-10 dimethicone, PEG-12 dimethicone, and PEG-14 dimethicone), and polyether-modified silicones expressed by the general formula (13) and known as the INCI name as polysilicone-13:

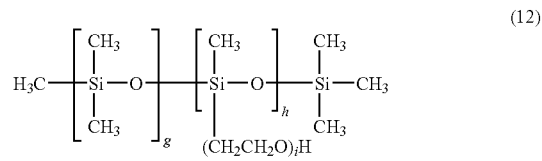

(12)

(in the formula, g and h denote numbers of 1 to 1,000, and i denotes a number of 1 to 2,000),

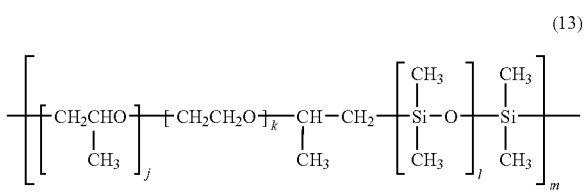

(13)

(in the formula, j, k and l denote numbers of 1 to 1,000, and m denotes a number of 1 to 2,000.)

(Silicones-4) Other Silicones

Examples of silicones other than the above include methylphenylpolysiloxane, fatty acid-modified silicones, alcohol-modified silicones, alkoxy-modified silicones, epoxy-modified silicones, fluorine-modified silicones, and alkyl-modified silicones.

In addition, such silicones being diluted or dispersed by volatile silicone, involatile silicone and the like, and those forming dispersion liquid particles in an aqueous surfactant can be also used.

Further, organic conditioning oils are preferably liquids with low viscosity and insoluble to water, and hydrocarbon oil, polyolefin, aliphatic esters, fatty acid amides, and a mixture thereof are included. In a measurement at 40° C., a viscosity of such an organic conditioning oil is preferably 1 to 200 mPa·s, more preferably 1 to 100 mPa·s, and even more preferably 2 to 50 mPa·s.

Examples of aliphatic esters include esters having hydrocarbon chains, which are derived from a fatty acid and an alcohol (e.g., monoester, polyvalent alcohol ester, and di- and tricarboxylate ester). A hydrocarbon group in these aliphatic esters may further have other compatible functional moieties such as an amide group and an alkoxy group (e.g., ethoxy or other bonding), or may covalently bind thereto. Specific examples of preferable aliphatic esters include isopropyl myristate and octyldecyl myristate.

Examples of aliphatic amides include amides having a hydrocarbon chain, which is derived from a fatty acid and alkylamine or alkanolamine. A hydrocarbon group in these aliphatic amides may further have other compatible functional moiety such as an amide group and an alkoxy group (e.g., ethoxy or other bonding), or may covalently bind thereto. Specific examples of preferable aliphatic amides include oleic acid diethanolamide, lauric acid diethanolamide, palm fatty acid amide, and palm fatty acid diethanolamide.

As a conditioning polymer, a cationic polymer is preferable, and can further contain anionic, nonionic and/or amphoteric polymer. Any anionic counter ion of a cationic polymer may be used if the cationic polymer is in a state of being dissolved and the counter ion is physically and chemically compatible with an essential component of the hair dyeing composition, or as long as performance, stability or visual appearance of a product is not damaged. Examples of such a counter ion include halide ion (e.g., chloride ion, fluoride ion, bromide ion, and iodide ion), sulfate ion, methyl sulfate ion and a mixture thereof. Examples of cationic polymers include cationic polysaccharide (e.g., cationic cellulose derivative and cationic guar), a copolymer of a vinyl monomer having a protonated amine-substituent group or a quaternary ammonium-substituent group with an aqueous monomer, a vinylpyrrolidone copolymer, and cationic protein.

The hair dyeing composition of the present invention can further contain polyalkylene glycol, and an amount thereof is 0.005 to 1.5% by weight in the whole composition, preferably 0.025 to 1.2% by weight, more preferably 0.05 to 1% by weight, and even more preferably 0.1 to 0.5% by weight. Such polyalkylene glycol is compatible with the components (A) to (C) of the present invention, and is required not to significantly damage stability, visual appearance or performance of a product. Specific examples thereof include polyethylene glycol and polypropylene glycol, and may be a mixture of the both or may be a copolymer thereof with ethylene oxide and propylene oxide.

In the hair dyeing composition of the present invention, water and/or an organic solvent is used as a medium. Examples of the organic solvent include lower alkanols such as ethanol and 2-propanol, aromatic alcohols such as benzyl alcohol and benzyloxyethanol, polyols such as propylene glycol, 1,3-butanediol, diethylene glycol, and glycerin, cellosolves such as ethyl cellosolve, butyl cellosolve, and benzyl cellosolve, and carbitols such as ethyl carbitol and butyl carbitol.

The hair bleaching composition and the hair dyeing composition of the present invention can be added with other components generally used as cosmetics materials in addition to the above described components.

Examples of such an optional component include hydrocarbons, animal and vegetable fat and oils, higher fatty acids, permeation accelerators, cationic surfactants, natural or synthesized polymers, higher alcohols, ethers, amphoteric surfactants, nonionic surfactants, protein derivatives, amino acids, antiseptic agents, chelating agents, stabilizers, antioxidants, vegetable extracts, crude drug extracts, vitamins, pigments, fragrant materials, and ultraviolet absorbers.

The hair dyeing composition of the present invention is provided as a two-part type composed of the first part containing an alkali agent and the second part containing an oxidizing agent in the same manner as currently widely used oxidation type hair bleaches or dyes. Formulations of these first part and second part can be, for instance, liquid, emulsion, cream, gel, paste, mousse, and the like, and also can be a form of an aerosol.

A mixing ratio (weight ratio) of the first part and the second part of the hair dyeing composition of the present invention is preferably in the range of 1:0.5 to 1:3 from the viewpoint of practicality.

In the hair dyeing composition of the present invention, it is preferable that a pH (25° C.) of the first part is 8 to 12 and a pH (25° C.) of the second part is 2 to 5, and a pH after mixing the first part and the second part is 7.5 to 12, and it is preferable to be pH 8 to 11 from the viewpoints of a bleaching and hair dyeing effect and skin irritating properties. Examples of a pH adjuster include inorganic acids such as hydrochloric acid and phosphoric acid, organic acids such as citric acid, glycolic acid, and lactic acid, hydrochloride such as ammonium chloride and monoethanolamine hydrochloride, phosphate such as potassium dihydrogen phosphate and disodium hydrogen phosphate.

The hair dyeing composition of the present invention preferably has a viscosity such that liquid dripping hardly occurs when the first part and the second part are mixed and applied to the hair. Specifically, a viscosity measured using a B type rotation viscometer at 25° C. (rotor in use No. 3, 12 rpm, value after rotation for 1 minute) is preferably 2,000 to 100,000 mPa·s.

In order to carry out dyeing treatment to the hair by using the hair dyeing composition of the present invention, for instance, the first part and the second part of the hair dyeing composition of the present invention are mixed and the mixture is then applied to the hair at a temperature of 15 to 45° C., and leaving for an action time of 1 to 60 minutes, preferably 3 to 45 minutes, and the hair is washed and then dried.

EXAMPLES

Production Example 1

3-amino-1,2,2-triethylpiperidine (compound 1-II-13)

Dialkylation Step

A four-necked pear-shaped flask (3 L) was charged with 380 mL (1.14 mol) of a 3.0 M ethyl magnesium bromide/diethyl ether solution and stirred while cooling with ice in a nitrogen atmosphere. Then, a solution of 65.05 g (0.38 mol) of 1-ethylproline ethyl ester and 600 mL of toluene was dropped over about 1 hour so that the reaction solution was 15° C. or less. After completion of the dropping, the reaction solution was heated to 50° C. and stirred for 3 hours.

Thereto was added 600 g of a 10% aqueous ammonium chloride solution, and the organic layer was separated, and the aqueous layer was then further extracted with diisopropyl ether (500 mL×3). The organic layer combined was dried over sodium sulfate anhydride, and then the solvent was distilled off under reduced pressure to thereby obtain a yellow liquid. The obtained liquid was purified by distillation at reduced pressure (133.33 Pa, 90° C.) and 52.96 g (yield of 75%) of a desired product, a prolinol derivative, was thus obtained as a colorless liquid.

Halogenating Step

A 20 L-kolben was charged with 1050 g (5.66 mol) of the above prolinol derivative, 857 g (8.49 mol) of triethylamine, and 12 L of dichloromethane, and the mixture was stirred while cooling with ice in a nitrogen atmosphere. Then, 748 g (6.50 mol) of methane sulfonyl chloride was added dropwise. After completion of the dropping, the resultant was stirred at 40° C. for one day.

While cooling with ice, 9.2 kg of water was added thereto and extracted with dichloromethane (10 L×2). The organic layer combined was dried over sodium sulfate anhydride, and then the solvent was distilled off under reduced pressure to thereby obtain 820 g of a chloro product as a mixture of a pyrrolidine derivative (general formula (4)): a piperidine derivative (general formula (5))=4:1.

This product was used in the following azidation step without further performing purification.

Azidation Step

A kolben (20 L) was charged with 820 g (4.02 mol) of the above chloro product, 550 g (8.46 mol) of sodium azide and 12 L of DMF, and the mixture was stirred at 40° C. for 4 hours.

The reaction solution was added to 9 kg of ice water and then extracted with dichloromethane (12 L×3). The organic layer was dried over sodium sulfate anhydride and then the solvent was distilled off under reduced pressure to thereby obtain 1076 g of a crude product. The resultant crude product was purified by silica gel chromatography (dichloromethane:methanol=10:1), and 610 g of an azide product was obtained as a reddish brown liquid.

Reduction Step

An autoclave reaction vessel (20 L) was charged with 605 g (2.87 mol) of the above azide product, 8 L of methanol, and 136 g of 10% Pd/C (wet), and the mixture was stirred for 4 hours with replacing at hydrogen pressure of 0.5 MPa every 30 minutes.

A catalyst was removed by filtration, and then the filtrate was concentrated to thereby obtain 461 g of a crude product as a pale yellowish brown liquid. The crude product was purified by distillation at reduced pressure (533 Pa, 70° C.), and 55.3 g of a desired product, 3-amino-1,2,2-triethylpiperidine (compound 1-II-13, yield of 10%), was obtained as a colorless transparent liquid.

$^1$H NMR (400 MHz, CDCl$_3$, ppm): σ 0.83-0.87 (3H), 0.88-0.92 (3H), 0.95-0.99 (3H), 1.20 (2H), 1.32-1.84 (8H), 2.41-2.53 (3H), 2.57-2.63 (1H), 2.71-2.74 (1H) $^{13}$C NMR (400 MHz, CDCl$_3$, ppm): σ 61.20, 51.50, 45.00, 43.54, 29.02, 23.20, 22.36, 22.10, 15.66, 9.49, 7.82

Production Example 2

3-pyrrolidinyl-1,2,2-triethylpiperidine (compound 1-II-12)

N-Alkylation Step

A four-necked pear-shaped flask (500 mL) was charged with 15.00 g (0.08 mol) of 3-amino-1,2,2-triethylpiperidine obtained in Example 1, 35.00 g (0.16 mol) of 1,4-dibromobutane, 34.09 g (0.41 mol) of sodium hydrogen carbonate, and 150 mL of toluene, and the mixture was stirred at 100° C. for 24 hours.

Salt was eliminated by filtration, and the solvent was distilled off under reduced pressure to thereby obtain 38.94 g of a crude product as a yellow liquid. The crude product was purified by distillation at reduced pressure (33 Pa, 97-101° C.), and 13.31 g of a desired product, 3-pyrrolidinyl-1-2,2-triethylpiperidine (compound 1-II-12, yield of 70%), was obtained as a colorless transparent liquid.

$^1$H NMR (400 MHz, CDCl$_3$, ppm): σ 0.82-0.89 (6H), 0.95-0.99 (3H), 1.33-1.68 (10H), 1.76-1.95 (2H), 2.06-2.14 (1H), 2.28-2.34 (1H), 2.51-2.57 (2H), 2.62-2.70 (4H), 2.74-2.82 (1H) $^{13}$C NMR (400 MHz, CDCl$_3$, ppm): σ 63.63, 60.47, 50.76, 44.79, 43.74, 26.14, 23.76, 23.34, 20.90, 20.75, 15.05, 10.03, 7.31

Production Example 3

3-dimethylamino-1,2,2-triethylpiperidine (compound 1-II-16)

N-Alkylation Step

A four-necked pear-shaped flask (500 mL) was charged with 10.02 g (0.054 mol) of 3-amino-1,2,2-triethylpiperidine obtained in Example 1, 43.84 g (0.540 mol) of a 37% aqueous formaldehyde solution, and 24.89 g (0.541 mol) of formic acid, and the mixture was stirred at 80° C. for 9 hours.

While cooling with ice, 100 g of a 48% aqueous sodium hydroxide solution was added thereto and extracted with chloroform (100 mL×3). The organic layer was dried over sodium sulfate anhydride, and the solvent was distilled off under reduced pressure to thereby obtain 11.78 g of a crude product as a yellow liquid. The crude product was purified by distillation at reduced pressure (20 Pa, 58-59° C.), and 6.98 g of a desired product, 3-dimethylamino-1,2,2-triethylpiperidine (compound 1-II-16, yield of 61%), was obtained as a colorless transparent liquid.

$^1$H NMR (400 MHz, CDCl$_3$, ppm): σ 0.81-0.86 (3H), 0.88-0.91 (3H), 0.95-0.98 (3H), 1.33-1.70 (6H), 1.77-1.95 (2H), 2.06-2.18 (1H), 2.22 (6H), 2.28-2.35 (1H), 2.41-2.45 (1H), 2.62-2.65 (1H), 2.71-2.80 (1H) $^{13}$C NMR (400 MHz, CDCl$_3$, ppm): σ 64.18, 63.72, 44.84, 44.02, 43.77, 26.15, 23.28, 20.87, 19.49, 15.11, 10.00, 7.51

Production Example 4

3-dimethylamino-1,2,2-triethylpiperidine (compound 1-II-16)

Amination Step

A four-necked pear-shaped flask (500 mL) was charged with 14.04 g (0.07 mol) of 2-(1-chloro-1-ethylpropyl)methyl-1-ethylpyrrolidine, 54.26 g (0.48 mol) of a 40% aqueous dimethylamine solution, and 100 mL of ethanol, and the mixture was stirred at 40° C. for 44 hours.

After extracting with chloroform (100 ml×3), the organic layer was dried over sodium sulfate anhydride, and then the solvent was distilled off under reduced pressure to thereby obtain 9.35 g of a crude product as a yellow liquid. The obtained crude product was purified by silica gel chromatography (n-hexane:ethyl acetate=8:1) and 4.16 g (compound 1-II-16, yield of 28%) of a desired product, 3-dimethylamino-1,2,2-triethylpiperidine, was thus obtained as a colorless transparent liquid.

Reference Examples 1 to 3

Solutions shown in the following tables were prepared in a glass container using synthesized melanin (made by Sigma-Aldrich Co.), and light absorption (600 nm) after 30 minutes was measured by a spectrometer (U-3300, manufactured by Hitachi, Ltd.) to find decomposition ratios (bleaching ratio) of the synthesized melanin. The decomposition ratio of the synthesized melanin was favorable when any compound obtained in Production Examples 1 to 3 was used, as compared with Comparative Reference Example 1.

TABLE 1

| (g) | Reference Example 1 | Reference Example 2 | Reference Example 3 | Comparative Reference Example 1 |
|---|---|---|---|---|
| 0.1 mass % synthesized melanin solution | 0.5 | 0.5 | 0.5 | 0.5 |
| 5 mass % aqueous monoethanol amine solution | 0.5 | 0.5 | 0.5 | 0.5 |
| 15 mass % aqueous hydrogen peroxide solution | 0.5 | 0.5 | 0.5 | 0.5 |
| Nonionic ion surfactant (1.4 mass % aqueous solution, SOFTANOL made by NIPPON SHOKUBAI CO., LTD.) | 0.5 | 0.5 | 0.5 | 0.5 |
| 1 mass % aqueous EDTA/4Na solution | 0.5 | 0.5 | 0.5 | 0.5 |
| 0.5 mass % aqueous solution of compound 1-II-13 | 0.5 | | | |
| 0.5 mass % aqueous solution of compound 1-II-12 | | 0.5 | | |
| 0.5 mass % aqueous solution of compound 1-II-16 | | | 0.5 | |
| Purified water | 2 | 2 | 2 | 2.5 |
| Total | 5 | 5 | 5 | 5 |
| Melanin bleaching ratio (%) | 81.6 | 78.3 | 75.8 | 70.3 |

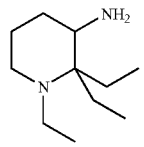

Compound 1-II-13

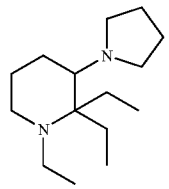

Compound 1-II-12

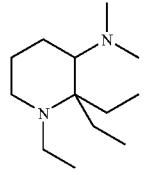

Compound 1-II-16

Example 1 and Comparative Examples 1 to 3

The first part shown in Table 2 and the second part shown in Table 3 were prepared, and when these agents were used in combination, bleaching properties and the feeling to the touch were evaluated.

TABLE 2

| First part (wt %) | Example product A | Comparative product B | Comparative product C |
|---|---|---|---|
| Compound 1-II-12 | 1.7 | — | — |
| Compound X | — | — | 1.3 |
| Ammonia (28 wt %) | 7.5 | 7.5 | 7.5 |
| EDTA-4Na | 0.1 | 0.1 | 0.1 |
| Propylene glycol | 4 | 4 | 4 |
| Stearyl trimonium chloride | 5 | 5 | 5 |
| CETETH-40 | 2.5 | 2.5 | 2.5 |
| Stearyl alcohol | 8 | 8 | 8 |
| Ammonium chloride | 0.5 | 0.5 | 0.5 |
| Purified water | Balance | Balance | Balance |
| pH | 10.2 | 10.2 | 10.2 |
| Total | 100 | 100 | 100 |

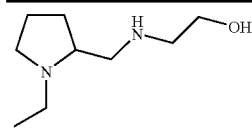

Compound X (Comparative compound)

TABLE 3

| Second part (wt %) | A | B |
|---|---|---|
| Hydrogen peroxide (35 wt %) | 17 | 23.7 |
| Methylparaben | 0.1 | 0.1 |
| Phosphoric acid | Amount for adjusting pH to 3.5 | Amount for adjusting pH to 3.5 |
| Purified water | Balance | Balance |
| Total | 100 | 100 |

(Treatment Method)

The first part and the second part were mixed in a mixing ratio (the first part:second part) shown in Table 4, and the resultant was applied to a tress of black hair in a bath ratio (agent:hair)=1:1. After leaving at 30° C. for 30 minutes, the hair tress was rinsed with water at 40° C., washed with a commercially available shampoo and rinsed with water, and a commercially available conditioner was applied, and the hair tress was then rinsed with water, wiped with a towel and dried.

[Evaluation of Bleaching Properties]

Brightness of a tress of hair bleached in accordance with the present bleaching steps was measured by the CIE color specification system ($L^*$, $a^*$, $b^*$) using a color-difference meter (color-difference meter CR-400 manufactured by Konica Minolta Sensing, Inc.) and $\Delta b^*$ was calculated according to the following formula. The larger $\Delta b^*$ indicated, the more excellent the bleaching properties are. Results are shown in Table 4.

$$\Delta b^* = b^*_2 - b^*_1$$

($b^*_1$ denotes a $b^*$ value before bleaching and $b^*_2$ demotes a $b^*$ value after bleaching)

[Evaluation of the Feeling to the Touch]

Fingers were through in the hair tress bleached in accordance with the present bleaching steps, and the feeling of catching fingers, friction, and roughness were scored according to the following criterion so as to evaluate the feeling to the touch. Results are shown in Table 4.

A: There is a little feeling of catching fingers, but no feelings of friction and roughness.

B: There is a little feeling of catching fingers, and there are also feelings of friction and roughness.

C: There are feelings of catching fingers, friction and roughness.

TABLE 4

|  | Example | Comparative Example | | |
|---|---|---|---|---|
|  | 1 | 1 | 2 | 3 |
| First part (mixing ratio) | A (1.0) | B (1.0) | C (1.0) | C (1.0) |
| Second part (mixing ratio) | A (1.5) | A (1.5) | A (1.5) | B (1.5) |
| pH (during mixing) | 9.6 | 9.8 | 9.7 | 9.5 |
| Bleaching properties ($\Delta b^*$) | 7.3 | 5.2 | 5.6 | 7.3 |
| Evaluation score of feeling to the touch | A | A | A | C |

According to Table 4, Example 1 in which a nitrogen-containing compound of a component (a) is used is excellent with respect that both of bleaching properties and feeling to the touch are preferable. Comparative Example 1 in which a nitrogen-containing compound is not used as the first part and Comparative Example 2 in which a nitrogen-containing compound different from the component (a) is used were both inferior in bleaching properties. Comparative Example 3 in which an amount of hydrogen peroxide of the second part is increased so as to have equivalent bleaching properties to Example 1 had a poor score in the feeling to the touch.

Example 2 and Comparative Example 4

The first part shown in Table 5 was prepared and evaluation of dyeing properties was performed.

[Evaluation of Dyeing Properties]

The first part shown in Table 5 and the second part A shown in Table 3 were respectively mixed in a mixing ratio of 1:1.5 (pH is 9.8 upon mixing), and the resultant was applied to a tress of white hair in a bath ratio (agent:hair)=1:1. After leaving at 30° C. for 50 minutes, the hair tress was rinsed with water at 40° C., washed with a commercially available shampoo and rinsed with water, and a commercially available conditioner was applied, and the hair was then rinsed with water, wiped with a towel and dried.

A color tone of the hair tress dyed in accordance with the present hair dyeing steps was measured by the CIE color specification system (L*, a*, b*) using a color-difference meter (color-difference meter CR-400 manufactured by Konica Minolta Sensing, Inc.) and $\Delta E^*$ was calculated according to the following formula. A larger $\Delta E^*$ indicates more excellent dyeing properties. Results are shown in Table 5.

$$\Delta E^* = \sqrt{(L^*_2 - L^*_1)^2 + (a^*_2 - a^*_1)^2 + (b^*_2 - b^*_1)^2}$$ [Mathematical Formula 1]

($L^*_1$, $a^*_1$ and $b^*_1$ denote measured values before dyeing, and $L^*_2$, $a^*_2$ and $b^*_2$ denote measured values after dyeing)

TABLE 5

| First part (wt %) | Example 2 | Comparative Example 4 |
|---|---|---|
| Compound 1-II-12 | 1 | — |
| Compound X | — | 1 |
| Paraamino phenol | 0.4 | 0.4 |
| Paraamino-ortho-cresol | 0.5 | 0.5 |

TABLE 5-continued

| First part (wt %) | Example 2 | Comparative Example 4 |
|---|---|---|
| Ammonia (28 wt %) | 7.5 | 7.5 |
| Propylene glycol | 4 | 4 |
| Stearyl trimonium chloride | 5 | 5 |
| CETETH-40 | 2.5 | 2.5 |
| Stearyl alcohol | 8 | 8 |
| Amodimethicone*[1] | 3 | 3 |
| Sodium sulfite | 0.5 | 0.5 |
| Ascorbic acid | 0.5 | 0.5 |
| Ammonium chloride*[2] | q.s. | q.s. |
| EDTA-4Na | 0.1 | 0.1 |
| Purified water | Balance | Balance |
| Total | 100 | 100 |

*[1]SM8704C, Dow Corning Toray Co., Ltd.
*[2]amount for adjusting pH to 10

TABLE 6

|  | Example 2 | Comparative Example 4 |
|---|---|---|
| L* | 49.5 | 55.1 |
| a* | 25.2 | 21.8 |
| b* | 36.6 | 35.5 |
| Dyeing properties ($\Delta E^*$) | 36 | 30 |

Example 2 is excellent with respect to showing preferable dyeing properties according to a $\Delta E^*$ value shown in Table 6, as compared with the comparative example (Comparative Example 4) in which the formulation is common except for a nitrogen-containing compound.

Formulation Examples

Formulation examples of the first part are shown in Tables 7 and 8. These are used by combining with the second part that is generally used (pH is 9.9 when mixed with the second part A in a weight ratio of 1:1).

TABLE 7

| First part (wt %) | Formulation Examples | | | |
|---|---|---|---|---|
|  | 1 | 2 | 3 | 4 |
| Compound 1-II-1 | 1 | — | — | — |
| Compound 1-II-13 | — | 0.75 | 0.5 | — |
| Compound 1-II-12 | — | — | 0.5 | — |
| Compound 1-II-16 | — | — | — | 3 |
| Paraamino phenol | 0.3 | 0.1 | — | 0.1 |
| 2-hydroxyethyl-p-phenylenediamine sulfate | 0.1 | — | 0.2 | — |
| Toluene-2,5-diamine sulfate | 0.2 | — | 0.3 | — |
| 5-amino-ortho-cresol | 0.1 | 0.1 | — | — |
| Metaamino phenol | 0.2 | — | 0.3 | 0.1 |
| HC blue 2 | — | 0.5 | — | — |
| Basic yellow 57 | — | — | 0.1 | 0.1 |
| Red No. 106 | 0.1 | — | — | — |
| Stearyl alcohol | 8 | 8 | 8 | 8 |
| COCAMIDE DEA | 4.5 | 4.5 | 4.5 | 4.5 |
| Glyceryl stearate (SE) | 1.3 | 1.3 | 1.3 | 1.3 |
| CETEARETH-30 | 4 | 4 | 4 | 4 |
| Sodium lauryl sulfate | 1 | 1 | 1 | 1 |
| Oleic acid | 2 | 2 | 2 | 2 |
| Propylene glycol | 1.5 | 1.5 | 1.5 | 1.5 |
| PEG-9 dimethicone*[3] | 1.5 | — | 1.5 | 1.5 |
| Hydrolyzed keratin | 0.5 | 0.5 | 0.5 | 0.5 |
| Panthenol | 0.8 | 0.8 | 0.8 | 0.8 |
| Ammonia (28 wt %) | 6 | 3 | 1 | — |
| Ethanolamine | — | 3 | 4 | 5 |

TABLE 7-continued

| First part (wt %) | Formulation Examples | | | |
|---|---|---|---|---|
| | 1 | 2 | 3 | 4 |
| EDTA-4Na | 0.5 | 0.5 | 0.5 | 0.5 |
| Ammonium chloride*4 | q.s. | q.s. | q.s. | q.s. |
| Purified water | Balance | Balance | Balance | Balance |
| Total | 100 | 100 | 100 | 100 |

*3KF-6005, Shin-Etsu Chemical Co., Ltd.
*4Amount for adjusting pH to 10

TABLE 8

| (wt %) | Formulation Examples | | | | |
|---|---|---|---|---|---|
| | 5 | 6 | 7 | 8 | 9 |
| Compound 1-II-12 | 0.5 | — | — | — | — |
| Compound 1-II-1 | 0.5 | 2 | — | — | — |
| Compound 1-I-1 | — | — | 1.5 | — | — |
| Compound 1-I-2 | — | — | — | 0.5 | — |
| Compound 1-I-11 | — | — | — | — | 0.8 |
| Toluene-2,5-diamine sulfate | 0.1 | 0.1 | 0.2 | — | 0.4 |
| 5-amino-ortho-cresol | 0.1 | 0.1 | 0.2 | — | 0.2 |
| HC blue 2 | 0.05 | — | — | 0.08 | 0.03 |
| Basic yellow 57 | 0.05 | — | 0.1 | 0.1 | — |
| Red No. 106 | — | 0.1 | 0.1 | — | — |
| Ethanol | 10 | 10 | 10 | 10 | 10 |
| Propylene glycol | 10 | 10 | 10 | 10 | 10 |
| Oleic acid | 10 | 10 | 10 | 10 | 10 |
| Oleamide DEA | 8 | 8 | 8 | 8 | 8 |
| Oleyl alcohol | 2 | 2 | 2 | 2 | 2 |
| CETETH-20 | 10 | 10 | 10 | 10 | 10 |
| PEG-9 dimethicone*5 | 1.5 | 1.5 | 1.5 | 1.5 | 1.5 |
| Ammonia (28 wt %) | 8 | 3 | 3 | 3 | 3 |
| Ethanolamine | — | 3 | 3 | 3 | 3 |
| EDTA-4Na | 0.1 | 0.1 | 0.1 | 0.1 | 0.1 |
| Ammonium chloride*6 | q.s | q.s | q.s | q.s | q.s |
| Purified water | Balance | Balance | Balance | Balance | Balance |
| Total | 100 | 100 | 100 | 100 | 100 |

*5KF-6005, Shin-Etsu Chemical Co., Ltd.
*6Amount for adjusting pH to 10

The invention claimed is:

1. A hair dyeing composition, comprising a first part comprising a component (a) and a second part comprising a component (b), wherein a pH upon use is 7.5 to 12:

(a) a nitrogen-containing compound expressed by the following general formula (1) or a salt thereof:

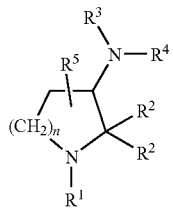

(1)

wherein n denotes an integer of 1 or 2, each of $R^1$ and $R^3$ to $R^5$ independently represents a hydrogen atom, a hydroxy group, or an alkyl group, an alkenyl group, an alkynyl group, a cyclic hydrocarbon group, an aralkyl group or a cyanated alkyl group each having 12 or less carbon atoms, or a 5 to 7 membered-ring saturated or unsaturated heterocyclic group, two of $R^2$ may be the same or different, and each represents a hydroxy group, —R or —OR, wherein R represents an alkyl group, an alkenyl group, an alkynyl group, a cyclic hydrocarbon group, an aralkyl group or a cyanated alkyl group each having 12 or less carbon atoms, or a 5 to 7 membered-ring saturated or unsaturated heterocyclic group, wherein $R^1$ to $R^5$ may further have one or more substituents selected from the group consisting of a hydroxy group, an amino group, an alkyl group, a cyclic hydrocarbon group, an aralkyl group, a heteroaryl group, an alkoxy group, an ester group, and a cyanated alkyl group each having 8 or less carbon atoms, and wherein two or more of $R^1$ to $R^5$ may be taken together to form a saturated or unsaturated 3 to 8 membered-ring, and the ring may have a substituent selected from the group consisting of a hydroxy group, and an alkyl group and a cyclic hydrocarbon group which have 12 or less carbon atoms and optionally may have a substituent; and (b) an oxidizing agent.

2. The hair dyeing composition according to claim 1, wherein, in the general formula (1), $R^1$ represents a hydrogen atom, or an alkyl group or a cyclic hydrocarbon group each having 12 or less carbon atoms, two of $R^2$ may be the same or different alkyl group or cyclic hydrocarbon group each having 12 or less of carbon atoms, $R^3$ and $R^4$ each independently represents a hydrogen atom, or an alkyl group or a cyclic hydrocarbon group each having 12 or less carbon atoms, or the both may be taken together to form a nitrogen-containing saturated 5 or 6 membered-ring, and $R^5$ represents a hydrogen atom, a hydroxy group, or an alkyl group or a cyclic hydrocarbon group each having 12 or less carbon atoms.

3. The hair dyeing composition according to claim 1 or 2, wherein the first part comprises an oxidative dye intermediate.

4. The hair dyeing composition according to claim 1, wherein the first part comprises a direct dye.

5. A method of hair dyeing, comprising the steps of:

mixing the first part and the second part of the hair dyeing composition according to claim 1 immediately before use;

applying a mixture of the first part and a second part to the hair; and leaving the hair for 1 to 60 minutes, and then rinsing the hair.

* * * * *